United States Patent
Licitra et al.

(10) Patent No.: US 9,995,676 B2
(45) Date of Patent: Jun. 12, 2018

(54) METHOD AND DEVICE FOR THE PREPARATION AND OPTICAL ANALYSIS OF A SOLID SAMPLE SUBJECTED TO A CONTROLLED ENVIRONMENT, BY MULTIPLE INTERNAL REFLECTION INFRARED SPECTROSCOPY

(71) Applicant: COMMISSARIAT A L'ENERGIE ATOMIQUE ET AUX ENERGIES ALTERNATIVES, Paris (FR)

(72) Inventors: Christophe Licitra, Grenoble (FR); Nevine Rochat, Saint Egreve (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 90 days.

(21) Appl. No.: 14/581,806

(22) Filed: Dec. 23, 2014

(65) Prior Publication Data

US 2015/0177130 A1 Jun. 25, 2015

(30) Foreign Application Priority Data

Dec. 23, 2013 (FR) ..................................... 13 63432

(51) Int. Cl.
- *G01N 21/3563* (2014.01)
- *G01N 21/552* (2014.01)
- *G01N 1/28* (2006.01)

(52) U.S. Cl.
CPC ....... *G01N 21/3563* (2013.01); *G01N 21/552* (2013.01); *G01N 1/2813* (2013.01)

(58) Field of Classification Search
CPC ................................................. G01N 21/3563
See application file for complete search history.

(56) References Cited

U.S. PATENT DOCUMENTS 3,478,206 A * 11/1969 Gaglione ............. G01N 21/552
250/428
4,508,832 A 4/1985 Carter et al.
(Continued)

FOREIGN PATENT DOCUMENTS

DE 19612877 9/1997
EP 0209489 1/1987
(Continued)

OTHER PUBLICATIONS

Olivier et al., Multiple internal reflection spectroscopy: a sensitive non-destructive probe for interfaces and nanometric layers, Feb. 2001, Materials Science in Semiconductor Processing, vol. 4, Iss. 1-3, pp. 15-18.*

(Continued)

*Primary Examiner* — David Porta
*Assistant Examiner* — Jeremy S Valentiner
(74) *Attorney, Agent, or Firm* — Norton Rose Fulbright US LLP

(57) ABSTRACT

A method of preparation and optical analysis of a solid sample by multiple internal reflection infrared spectroscopy comprising: obtaining a least one substrate that is transparent to infrared light and comprises at least a main front face and a main rear face; producing at least one solid sample on the main front face of the substrate; installing around at least one part of the sample an element comprising a chamber having an aperture that opens onto the solid sample and defines a leaktight interaction zone (Zi) in relation to the outside of the chamber; feeding the chamber with a fluid with controlled parameters to control the environment in the leaktight interaction zone; sending an infrared light beam through the substrate; and recovering the beam after it has undergone multiple internal reflections in the substrate.

30 Claims, 8 Drawing Sheets

(56) References Cited

U.S. PATENT DOCUMENTS

| | | | |
|---|---|---|---|
| 4,595,833 A | 6/1986 | Sting | |
| 4,602,869 A | 7/1986 | Harrick | |
| 5,035,504 A | 7/1991 | Milosevic et al. | |
| 5,220,401 A | 6/1993 | Milosevic et al. | |
| 5,452,083 A | 9/1995 | Wilks, Jr. et al. | |
| 5,616,922 A | 4/1997 | Reffner et al. | |
| 6,954,560 B2 | 10/2005 | Tolmachev et al. | |
| 7,956,328 B2 | 6/2011 | Sundaram et al. | |
| 9,366,601 B1 * | 6/2016 | Chen | G01N 1/00 |
| 2003/0094032 A1 * | 5/2003 | Baklanov | G01N 15/08 73/38 |

FOREIGN PATENT DOCUMENTS

| | | |
|---|---|---|
| GB | 2105058 | 1/1986 |
| WO | WO2000/036458 | 6/2000 |
| WO | WO2003/083458 | 10/2003 |
| WO | WO2005/047873 | 5/2005 |
| WO | WO2005/124300 | 12/2005 |

OTHER PUBLICATIONS

Harrick, N.J.: "Internal Reflection Spectroscopy", Book Chapter 4, Harrick Scientific Corporation (1967).

Olivier, M. et al: "Multiple internal reflection spectroscopy: a sensitive non-destructive probe for interfaces and nanometric layers", *Materials Science in Semiconductor Processing*, vol. 4, No. 1-3. (Feb. 6, 2001), pp. 15-18.

Rochat, Nevine et al: "Multiple internal reflection infrared spectroscopy using two-prism coupling geometry: A convenient way for quantitative study of organic contamination on silicon wafers", *Applied Physics Letters*, vol. 77, No. 14, (Oct. 2, 2000), pp. 2249-2251.

Olivier, M. et al: "Infrared Study of Hydrogen in Ultra-Thin Silicon Nitride Films Using Multiple Internal Reflection Spectroscopy (MIR) in 200 mm Silicon Wafers" *Physica Status Solidi*, vol. 175, (1999), pp. 137-143.

* cited by examiner

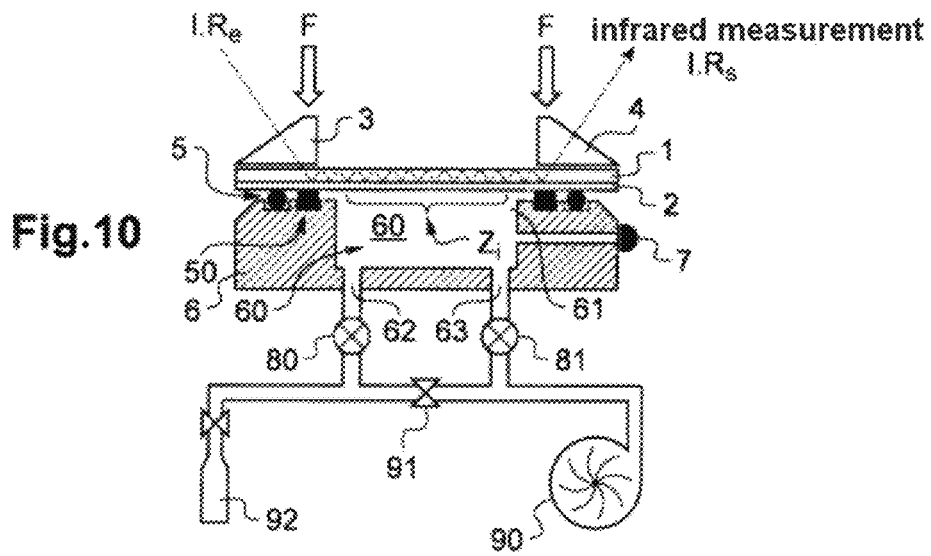
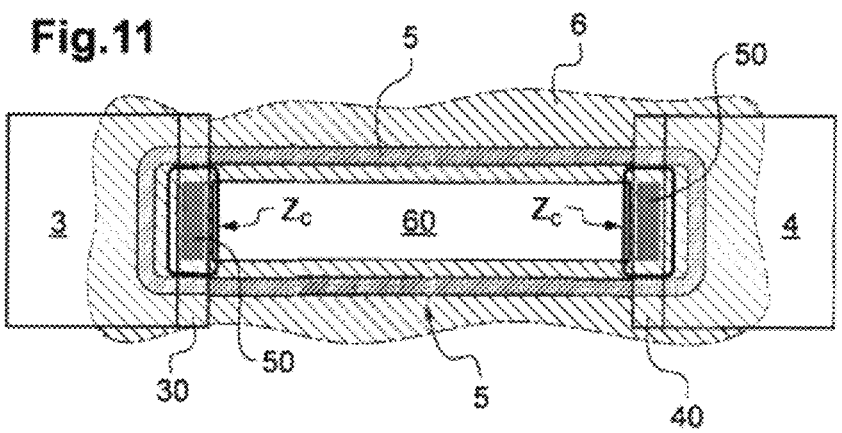
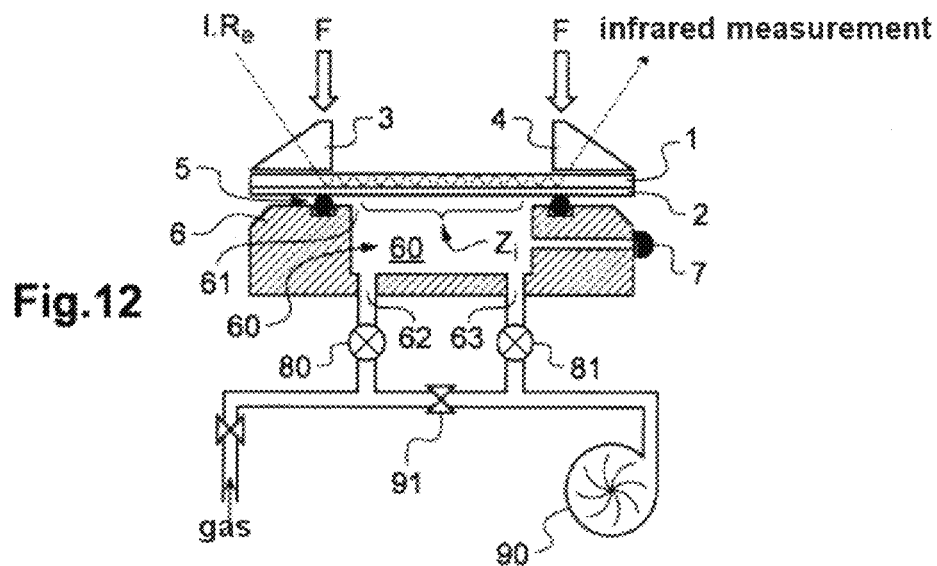

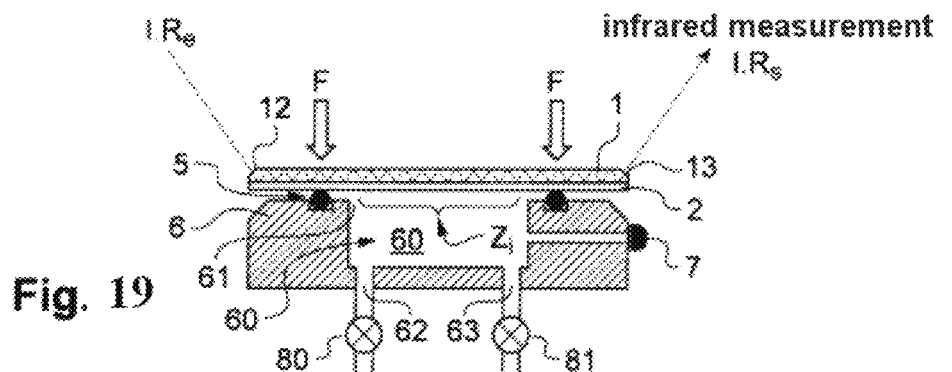
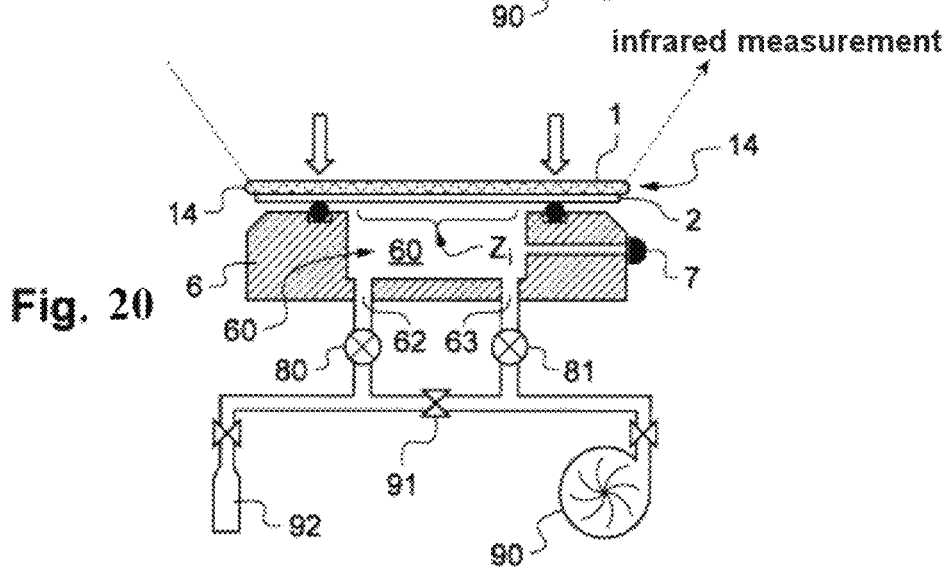
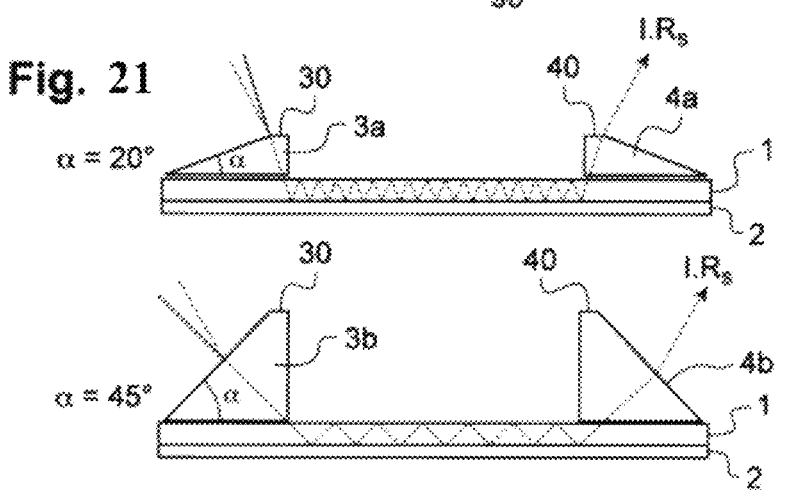

METHOD AND DEVICE FOR THE PREPARATION AND OPTICAL ANALYSIS OF A SOLID SAMPLE SUBJECTED TO A CONTROLLED ENVIRONMENT, BY MULTIPLE INTERNAL REFLECTION INFRARED SPECTROSCOPY

TECHNICAL FIELD

The present invention relates to a method and device for the preparation and optical analysis of a solid sample subjected by infrared spectroscopy to multiple internal reflections.

The invention is aimed at allowing non-destructive measurements of a solid sample on the one hand with high sensitivity and on the other hand which may be representative of the in-situ conditions to which the solid material(s) of the sample may be subjected.

The expression "infrared light" is understood to mean within the framework of the invention a light emitting in the infrared wavelength range, typically in the wave number range lying between 1500 and 9000 cm$^{-1}$.

The expression "solid sample" is understood to mean within the framework of the invention a surface preparation and/or conditioning of a substrate, for example cleaning, etching, etc. and/or at least one solid sample layer deposited on the substrate. When the solid sample is a layer, the latter can be continuous or discontinuous.

The expression "controlled environment" is understood to mean within the framework of the invention a fluidic environment in which it is possible to vary the parameters, such as pH, composition, pressure, temperature, humidity, etc. by controlling them.

The expression "prism" is understood to mean within the framework of the invention, the usual sense in the field of optics, namely a block of a material transparent to infrared light, typically obtained by cutting, preferably comprising three faces on a triangular base, two of which are at right angles to one another, and used in the guise of optical instrument used to refract light.

The expression "prism angle" is understood to mean within the framework of the invention the angle of aperture of the prism, that is to say the angle formed between the face through which the infrared light beam enters and the face opposite the rear face of the substrate, i.e. the face with which a minimum of gap is created.

The expression "bevel" is understood to mean within the framework of the invention the usual sense afforded in mechanics, namely a flat surface of the substrate, obtained by eliminating a sharp corner, also called chamfer.

The expression "optical coupling" is understood to mean within the framework of the invention the fact that an infrared light beam arriving at a prism and refracted by the latter can enter the substrate and undergo multiple internal reflections within it. An optical coupling zone according to the invention is therefore a zone through which the infrared light refracted initially by a prism can enter the substrate and undergo multiple internal reflections therein.

The expression "land" is understood to mean within the framework of the invention, the usual sense afforded in mechanics, namely a flat surface conferred on an object.

PRIOR ART

Diverse multiple internal reflection infrared spectroscopy measurement procedures for the optical analysis of a sample are already known. The infrared spectrum of a sample is established by passing an infrared light beam through a substrate transparent to the infrared radiation of the beam. The beam undergoes multiple reflections inside the substrate. The sample to be analyzed is in contact with the reflecting surface of the substrate or is itself the reflecting surface.

Publications [1] and [2] describe the analysis of a solid sample according to this principle, the multiple reflections being produced in a silicon substrate, the infrared light propagating in the substrate and being coupled in the substrate by two silicon prisms arranged on a main face of the substrate. The principle of light coupling and propagation disclosed in these publications makes it possible to increase the sensitivity of the measurement. The drawback of the device described in these publications is that it operates only in the atmosphere, and therefore does not allow measurements representative of in-situ conditions to which the material of the sample may be subjected.

Publication [3] discloses diverse multiple internal reflection configurations some of which may be used in a controlled environment, liquid or gaseous. The drawback of the configurations according to this publication is that the multiple internal reflections element can only be a part of the optical setup.

Patent applications and patents U.S. Pat. No. 4,602,869, U.S. Pat. No. 5,220,401, U.S. Pat. No. 5,035,504, WO03/083458A2, DE19612877C1, DE3227456A1, U.S. Pat. No. 5,452,083A, U.S. Pat. No. 6,954,560B2, WO200547873A2 and WO2005124300A1 describe the analysis by multiple internal reflection infrared spectroscopy of a sample in a liquid environment. In all these patent applications or patents, the sample to be analyzed can only be the liquid of itself.

U.S. Pat. No. 7,956,328B2 describes a system for optical analysis by infrared spectroscopy in which living cells are grafted onto a multiple internal reflections element and then subjected to a variable environment. The major drawback of the system disclosed is that the internal reflections element must be dismounted and then prepared before each measurement. The preparation operation, for example the deposition of a functionalization layer, is constrained by the shape and the dimensions of the internal reflections element and the latter must be changed for subsequent experiments.

The general aim of the invention is to propose an improvement in optical analysis of a solid sample by multiple internal reflection infrared spectroscopy, which alleviates at least part of the hereinabove mentioned drawbacks of the prior art, in particular which allows measurements of the sample in a controlled environment representative of in-situ conditions to which the solid material(s) of the sample may be subjected.

A particular aim of the invention is to propose a solution for the optical analysis of a solid sample which meets the general aim, which is simple to implement, reliable, which allows a large number of measurements on one and the same sample without having to modify all or part the elements of the optical analysis device and which allows fast installation of a given sample before its measurement.

DISCLOSURE OF THE INVENTION

Accordingly, the subject of the invention is primarily according to a first alternative, a method of preparation and optical analysis of a solid sample by multiple internal reflection infrared spectroscopy, the method comprising the following steps:

a/ production of at least one solid sample on one of the main faces, the so-called front face, of a substrate transparent to an infrared light, b/ installation of at least one part of at least one pair of prisms remote from one another, on the other of the main faces, the so-called rear face of the substrate, the angle of the prisms being suitable for allowing multiple internal reflections in the substrate of an infrared light refracted by one of the prisms, c/ leaktight installation on the substrate, around at least one part of the sample, of an element comprising a chamber exhibiting an aperture, so that the aperture opens out onto the solid sample while defining a leaktight interaction zone in relation to the outside of the chamber, d/ feeding of the chamber with a fluid with controlled parameters so as to control the environment in the leaktight interaction zone, e/ sending of an infrared light beam through one of the prisms of a pair, f/ recovery of the beam having undergone multiple internal reflections in the substrate and re-emitted by the other of the prisms of the pair.

According to a second alternative of the method according to the invention, step b/ is replaced with a step b'/ of beveling the edges of the substrate between the front face and the rear face, the angle of the bevels being suitable for allowing multiple internal reflections in the substrate of an infrared light refracted by one of the bevels, step e/ is replaced with a step e'/ of sending an infrared light beam through one of the beveled edges of the substrate, step f/ is replaced with a step f'/ of recovery of the beam having undergone multiple internal reflections in the substrate and re-emitted by the other of the beveled edges of the substrate.

According to a third alternative of the method according to the invention, step b/ or b'/ is replaced with a step b"/ of providing a substrate with at least two rounded edges between the front face and the rear face, the rounding of the edges being suitable for allowing multiple internal reflections in the substrate of an infrared light (I-Re) refracted by one of the edges, step e or e'/ is replaced with a step e"/ of sending an infrared light beam through one of the rounded edges of the substrate, step f or f/ is replaced with f"/ of recovery of the beam having undergone multiple internal reflections in the substrate and re-emitted by the other of the rounded edges of the substrate.

A substrate with rounded edges, provided according to step b"/, can be a silicon wafer arising directly from manufacture and which does not require any step properly speaking of fashioning of the edges by rounding. The substrate may also be one whose edges are fashioned to obtain the desired roundings.

Whatever the alternative, the surface state and the parallelism of the main faces of a substrate according to the invention must be such that it can allow multiple internal reflections within it without outward scatter. Preferably, the two main faces undergo polishing before production of the solid sample. Thus, the two main faces are advantageously polished and mutually parallel.

When the solid sample is a solid sample layer, its deposition can be effected on all or part of the front face of the substrate, that is to say by defining at least one leaktight zone of interaction with a controlled fluidic environment.

The setup according to the invention makes it possible to measure easily removable samples in contradistinction to the devices according to the prior art patents detailed in the preamble. This allows easy and economical preparation of multiple solid samples on conventional substrates, such as those produced by microelectronics methods.

The method according to the invention makes it possible to control the environment close to the solid sample surface. The interactions between the environment which can be variable but controlled and the sample are then analyzed by virtue of the optical measurement of the infrared beam having undergone multiple internal reflections within the substrate, each reflection at the surface of the sample which makes it possible to probe the solid material of the sample either by propagation of light directly in the solid sample, or by an evanescent wave which was established after the diopter where the total reflection takes place.

By virtue of the invention, one obtains the analysis of a solid sample on the one hand with high sensitivity and on the other hand which is representative of the in-situ conditions to which the solid material(s) of the sample may be subjected.

According to a first mode, the fluid feeding the chamber is a liquid whose temperature and/or pressure and/or pH and/or composition are/is controlled.

According to a second mode, the fluid feeding the chamber is a gas whose temperature and/or pressure and/or humidity factor and/or composition are/is controlled. According to this second mode, provision is advantageously made for a step comprising g/ of evacuating the chamber before step d/ of feeding with the gas.

According to a first variant, step d/ of feeding is carried out from a reservoir of liquid which evaporates in the chamber kept evacuated.

According to a second variant, step d/ of feeding is carried out with a gas with given humidity factor, controlled in the chamber.

According to a third variant, step d/ of feeding is carried out with reactive species, preferably a plasma, controlled in the chamber. The plasma can be generated in-situ in the chamber or in an off-site manner within an appropriate generator in fluidic communication with the chamber.

Step c/ of leaktight installation of the element advantageously comprises the clamping of a peripheral seal around the aperture against the front face of the substrate.

Advantageously also, step c/ of leaktight installation of the element comprising the clamping of a peripheral seal around the aperture against the front face of the substrate, the clamping of the seal making it possible simultaneously to bring the prisms to bear against the rear face of the substrate. Thus, in a way the seal has a dual-function since in addition to its first function of leaktightness between the chamber in which the environment is controlled and the outside, it allows effective clamping of the prisms while considerably decreasing the risk of breakage of the substrate and therefore of the sample.

Preferably, the prisms each comprising a land on their vertex, the clamping axes being aligned with the lands and the seal. The land is preferably parallel to the faces of the substrate. Thus, it is possible to advantageously align the clamping load along a direction in which the land, the zone of optical coupling between prism and substrate and the seal all lie.

According to an advantageous embodiment, step b/ consists in installing at least one part of two pairs of prisms, the angle of the prisms and/or the material of one pair being different from that (those) of the other pair, the distance between the two prisms of one pair being equal to that between the two prisms of the other pair, steps e/ and f/ are repeated twice consecutively, once with one of the pairs of prisms and the consecutive time with the other of the pairs of prisms.

According to this mode, the installation of two different pairs of prisms according to step b makes it possible to generate two different angles of propagation in the substrate and therefore two different optical paths. Thus, a measurement for each angle of propagation is carried out at each condition of environment in the chamber representative of an in-situ condition. Next, the measurement made with the smallest angle of propagation is adjusted by that made with the largest angle so as to obtain the absolute (auto-referenced) measurement of the infrared absorption of the sample layer. Such a mode makes it possible to carry out absolute measurements of absorption by subtracting at each condition representative of an in-situ condition, two measurements having a different optical path.

The subject of the invention is also, according to another of its aspects and according to a first alternative, a device for the preparation and optical analysis of a solid sample by multiple internal reflection infrared spectroscopy comprising:
  a substrate exhibiting two main faces, one a so-called front face and the other a so-called rear face, and exhibiting at least one solid sample on the front face;
  at least one pair of prisms arranged remote from one another and at least in part on the rear face of the substrate, the angle of the prisms being suitable for allowing multiple internal reflections in the substrate of an infrared light refracted by one of the prisms;
  an element comprising a chamber exhibiting an aperture opening out onto the solid sample while defining a leaktight interaction zone in relation to the outside of the chamber, the chamber being suitable for being fed with a fluid with controlled parameters so as to control the environment in the leaktight interaction zone.

The substrate can be made of a material of refractive index equal to that of the prisms. The best effectiveness of optical coupling is thus obtained.

Alternatively, the substrate is made of a material of different refractive index from that of the prisms. According to this variant, care is taken that the angle of the prisms makes it possible to obtain the condition of total reflection in the substrate of different index.

According to an advantageous variant embodiment, each of the prisms comprises a land on its vertex.

According to an advantageous embodiment, the device comprises two pairs of prisms, the angle of the prisms and/or the material of one pair being different from that (those) of the other pair, the distance between the two prisms of one pair being equal to that between the two prisms of the other pair.

The angle ($\alpha$) of the prisms of a pair lying between 20 and 60°. With this range of values, best account is taken of the divergence of the infrared beam, of the presence of a surface layer of different index from air while preserving a large number of internal reflections.

The subject of the invention is also, according to a second alternative, a device for the preparation and optical analysis of a solid sample by multiple internal reflection infrared spectroscopy comprising:
  a substrate exhibiting two main faces, one a so-called front face and the other a so-called rear face, and exhibiting at least one solid sample on the front face, the substrate exhibiting bevels between the front face and the rear face, the angle of the bevels being suitable for allowing multiple internal reflections in the substrate of an infrared light refracted by one of the bevels,
  an element comprising a chamber exhibiting an aperture opening out onto the solid sample while defining a leaktight interaction zone in relation to the outside of the chamber, the chamber being suitable for being fed with a fluid with controlled parameters so as to control the environment in the leaktight interaction zone.

The subject of the invention is also, according to a third alternative, a device for the preparation and optical analysis of a solid sample by multiple internal reflection infrared spectroscopy comprising:
  a substrate exhibiting two main faces, one a so-called front face and the other a so-called rear face, and exhibiting at least one solid sample on the front face, the substrate exhibiting at least two rounded edges between the front face and the rear face, the rounding of the edges being suitable for allowing multiple internal reflections in the substrate of an infrared light refracted by one of the edges,
  an element comprising a chamber exhibiting an aperture opening out onto the solid sample while defining a leaktight interaction zone in relation to the outside of the chamber, the chamber being suitable for being fed with a fluid with controlled parameters so as to control the environment in the leaktight interaction zone.

According to this third alternative, the substrate can advantageously be a silicon wafer arising directly from manufacture with the rounded edges as such.

The material of the substrate is preferably chosen from among silicon (Si), germanium (Ge), zinc selenide (ZnSe), zinc sulfide (ZnS), sapphire, III-V materials such as GaAs, or InP, chalcogenides or metal oxides. The system will be easily suited to all these substrates, preferably by using prisms produced from the same material as the substrate implemented or from a material of close index so as to obtain good optical coupling.

According to a preferred variant, the substrate is made of silicon, preferably in the form of a wafer. Silicon has the advantage of being transparent in the infrared range lying between 1500 to 9000 cm$^{-1}$. In microelectronics, silicon is available in the form of wafers of various diameters whose faces are parallel. The 300-mm diameter wafers currently being manufactured have their two main faces parallel and polished and are therefore optimal for implementing the method according to the invention.

Preferably also, the material of the prisms is chosen from among silicon, germanium (Ge), zinc selenide (ZnSe), zinc sulfide (ZnS) or any material transparent in the infrared, which can be fashioned in the form of a prism and which exhibits an optical index compatible with the index of the substrate in the infrared.

According to an advantageous variant embodiment, there is provided a peripheral seal housed in a peripheral groove of the element, around the aperture.

The lands are preferably arranged plumb with the peripheral seal.

According to a variant, the lands can be arranged offset from the peripheral seal and each plumb with a bearing surface. This bearing surface can be situated between the chamber aperture and the O-ring seal. This bearing surface can be produced with a piece made of rigid or compressible material. According to this variant, the leaktightness and the clamping of the prisms is in a way decoupled.

According to an advantageous embodiment, the device according to the invention comprises one or more sensors suitable for measuring the pressure and/or the temperature and/or the pH and/or the humidity and/or the composition inside the chamber. Thus, it is possible to precisely control the various parameters of the fluid injected into the chamber, doing so in an easy manner.

The device preferably comprises a pumping system suitable for evacuating the chamber.

The device can also comprise an illumination system, preferably ultraviolet or infra-red, for the inside of the chamber.

According to a particularly advantageous embodiment, the substrate and the pairs of prisms are made of silicon, the angle ($\alpha$) of the prisms of one pair being equal to 20°, that of the prisms of the other pair being equal to 45°.

The subject of the invention is finally the application of the method or of the device which have just been described, for the analysis of a sample of porous material, such as SiOCH subjected to an environment with controlled humidity factor. This application is advantageous for the microelectronics industry. Indeed, porous materials exhibit variations of chemical properties during the methods of integration into electronic chips that it is necessary to analyze. For example, changes in hydrophobicity may occur degrading the insulating properties of the material. These changes can be studied by measuring the wavelength peaks characteristic of water with the aid of multiple internal reflection infrared spectroscopy whilst the porous material is subjected to humidity conditions that vary but are controlled according to the method of the invention.

DETAILED DESCRIPTION

Other advantages and characteristics of the invention will emerge better on reading the detailed description of the invention given by way of nonlimiting illustration with reference to the following figures among which:

FIG. 10 is a cross-sectional schematic view of a device according to the first alternative of the invention showing the clamping of leaktightness and of optical coupling between a prism and the substrate according to a second variant of the invention;

FIG. 11 is a view from above of the device according to FIG. 10 showing the relative arrangement between the various components of a device according to the invention;

FIG. 12 is a schematic side view showing a device according to the first alternative of the invention and making it possible to subject the solid sample layer to a controlled gas environment;

FIG. 19 is a schematic side view showing a device according to the second alternative of the invention and making it possible to subject the solid sample layer to a controlled gas environment;

FIG. 20 is a schematic side view showing a device according to the third alternative of the invention and making it possible to subject the solid sample layer to a controlled gas environment;

FIG. 21 is a schematic side view showing a device according to the first alternative of the invention and according to an advantageous embodiment allowing an absolute measurement of infrared luminous absorption.

In the description which follows and in the patent application as a whole, the terms "input", "output" are used with reference to the direction of an infrared light beam from its emission to its reception after having undergone the multiple internal reflections in a substrate in accordance with the invention. Thus, the infrared beam is firstly refracted by an input prism, undergoes multiple internal reflections within a substrate and exits therefrom while being refracted by an output prism.

The terms "top", "bottom", "vertex", "plumb", "upper", "lower" are used with reference to a device according to the invention in a configuration set up with a substrate horizontal and its rear face on the top. Thus, in such a configuration, a prism is atop the substrate itself above the chamber fed with controlled fluid. It goes without saying that other configuration setups are possible. For example, it is possible to have a configuration with a substrate and the prisms arranged vertical, the prisms then being on one vertical side of the substrate and the chamber on the other vertical side of the substrate.

It is specified that, in accordance with the invention, an infrared beam can be linearly polarized s-wise which is a direction perpendicular to the plane of incidence or p-wise which a direction parallel to the plane of incidence.

The various steps of preparation and optical analysis of a solid sample 2 by multiple internal reflection infrared spectroscopy according to the first alternative of the invention are described in relation to FIGS. 1A to 1E.

Figure 1A:
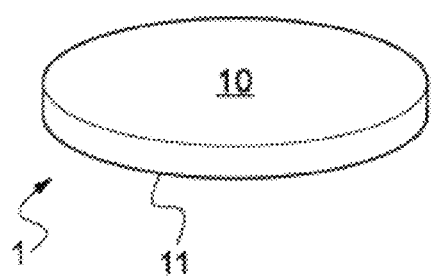
FIGS. 1A to 1E are schematic views illustrating the various steps of preparation and optical analysis of a solid sample according to the first alternative of the invention.

A substrate 1 with two main faces, i.e. a front face 10 and a rear face 11, is employed (FIG. 1A).

Figure 1B:
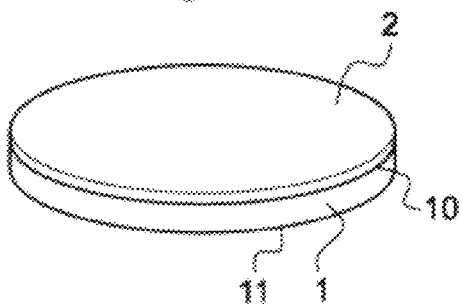
Figure 1C:
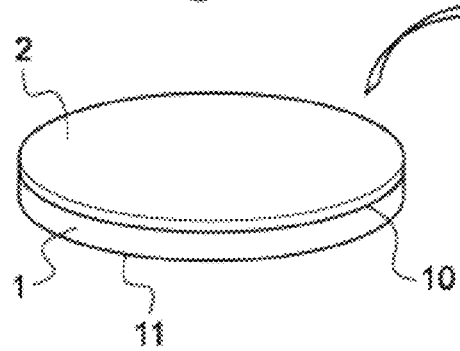

Next, a solid sample layer 2 for analysis is deposited on the front face 10 of the substrate 1 (FIG. 1B). Such a substrate 1 with the layer 2 can be produced easily and economically for example by virtue of the conventional methods of microelectronics.

Figure 1D:
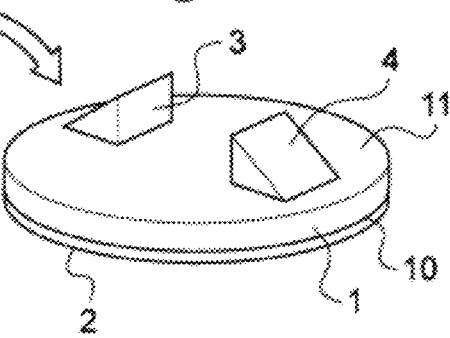

The substrate 1 is then turned over, in such a way that its rear face 11 is situated on top (FIG. 1D).

A pair of two prisms 3, 4 is then put in place directly in contact with the rear face 11 of the substrate 1, the prisms being arranged remote from one another (FIG. 1D). As illustrated, the prisms 3, 4 are advantageously blocks of right-angled triangular shape with the right angle at 90° to the rear face 11. The angle α of the prisms 3, 4 is chosen to allow an internal total reflection of the light on the faces 10, 11 of the substrate 1 supporting the solid sample 2. The faces 10, 11 of the substrate are parallel and polished.

Figure 6:
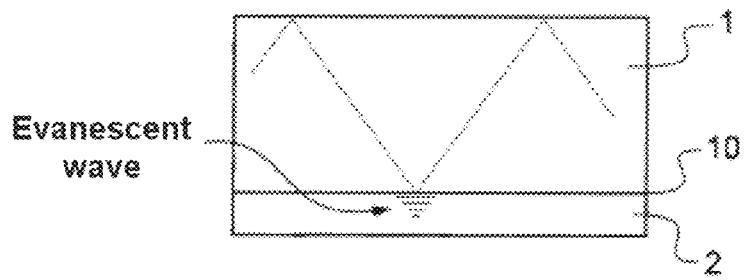
FIG. 6 is a schematic detail view showing the generation of an evanescent wave in a solid sample layer by the total reflection of an infrared wave in the substrate supporting the layer.

An infrared light I.Re entering the input prism 3 can be coupled and propagate in the substrate 1 which is optically transparent in the infrared spectral range of the incident light. At each reflection at the front surface 10 of the substrate, a wave probes the solid sample material 2 deposited on this surface 10 of the substrate 1 either by propagation of the light directly in the solid sample, or by an evanescent wave which is established after the diopter where the total reflection takes place. The diopter may be the interface between the substrate 1 and the sample layer 2 or else between the sample layer 2 and the outside environment, that is to say that which is controlled according to the invention. Stated otherwise, according to the optical indices of the substrate and of the layer(s) of sample present, the evanescent wave is established in the layers following the diopter where the total reflection takes place. In FIG. 6, a situation has been represented in which the evanescent wave is established at the interface between the front face 10 of the substrate 1 and the solid sample layer 2.

Figure 1E:
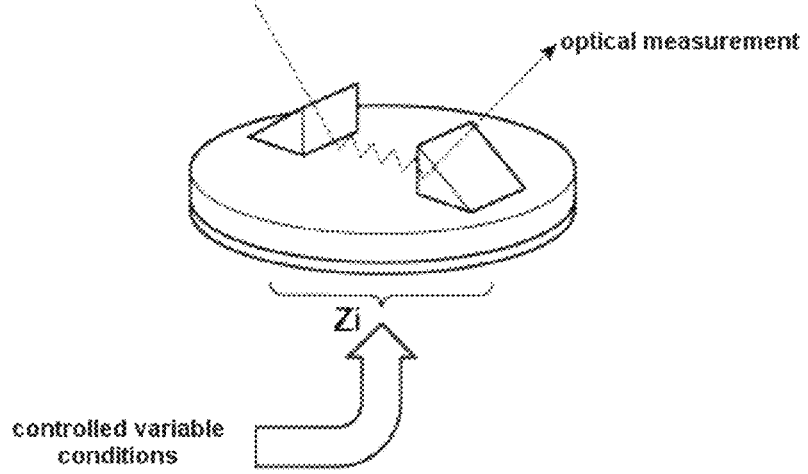

Once, this optical coupling has been obtained with the multiple internal reflections at least one part of the sample layer 2 is placed facing a chamber 60 making it possible to control the fluidic environment close to the surface of the layer 2. Thus, according to the invention the interactions between a controlled environment which can be variable and the sample 2 are then analyzed by virtue of the optical measurement by multiple internal reflections at the substrate 1 (FIG. 1E). The optical measurement is a measurement of transmittance ($T=I_{smp}/I_{ref}$) or of absorbance ($A=\log_{10}(1/T)$) of the beam on its exit I.Rs (Ismp) from the substrate 1 supporting the sample 2 involving a prior reference measurement (Iref) on a bare substrate for example. The value of the transmission Tr can be obtained as a percentage, on the basis of the following relation: $Tr=100*T$.

With two silicon prisms 3, 4 it is possible to couple an infrared light of wave number lying between 1500 and 9000 $cm^{-1}$, inside a silicon substrate 1 whose thickness is of the order of 800 µm in the case of a substrate in the form of a wafer of diameter 300 mm.

Various shapes of prisms may be suitable, the simplest being triangular with a right angle, as illustrated in FIGS. 1A to 1E.

According to an advantageous variant, each of the prisms 3, 4 exhibits a land at their vertex so as to be able to easily apply the force for clamping the prism against the rear face 11 of the substrate. All or part of the base of a prism 3, 4 may be placed in contact with the rear face 11.

Figure 2:
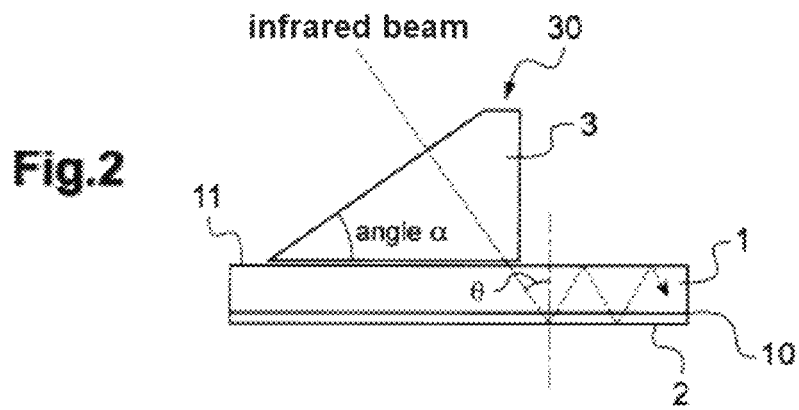
FIG. 2 is a cross-sectional schematic view of a part of a device according to the first alternative of the invention showing the multiple internal reflections within the substrate supporting the solid sample.

The angle α of the prisms 3, 4 is chosen to allow internal total reflections of the light on the two faces 10, 11 of the substrate as symbolized dashed in FIG. 2. These total internal reflections can occur if the angle of propagation θ between the beam at input I.Re and the normal to the substrate 1 is greater than a critical angle $θ_c$. For silicon of index $n_{Si}=3.42$ in the infrared, the critical angle of incidence $θ_c$ onwards of which there is total reflection at the silicon/air interface is about 17° ($θ_c=\arcsin(1/n_{Si})$). In order to take account of the divergence of the infrared beam, of the presence of a surface layer of different index from air while preserving a large number of internal reflections, prisms 3, 4 of angle α lying between 20° and 60° are preferably envisaged. In the case of normal incidence on an input prism 3, and if the prism 3 and the substrate 1 consist of one and the same material, the angles α and θ will be equal.

Figure 3:
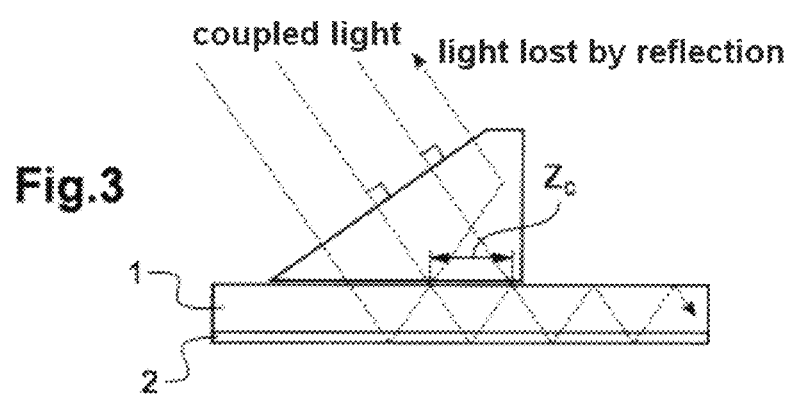
FIG. 3 is a schematic view similar to FIG. 2 showing the effective zone of optical coupling between a prism and the substrate in accordance with the invention.

To optimize the optical measurement with better effectiveness of optical coupling, the infrared beam is s-wise linearly polarized. An s polarization also makes it possible to limit the losses by reflection and the effects of change of polarization upon refraction in the prism. The critical point is the positioning of the infrared beam to obtain the coupling in the substrate. Indeed, only a small portion of the beam can pass into the substrate 1 and remain trapped there, thus defining an optical coupling zone Zc, as illustrated in FIG. 3. The width of such a coupling zone Zc is equal to $2*e*\tan θ$, e being the thickness of the substrate. For example, the width of a coupling zone Zc equals 923.8 µm for a silicon substrate 1 of thickness 800 µm and an angle of propagation θ of 30°. As illustrated in FIG. 3, the coupling zone Zc is situated close to the right angle of the prism 3.

A residual air gap e is present between each of the prisms 3, 4 and the substrate 1 on account of the irregularities present on the facing surfaces.

Figure 4:
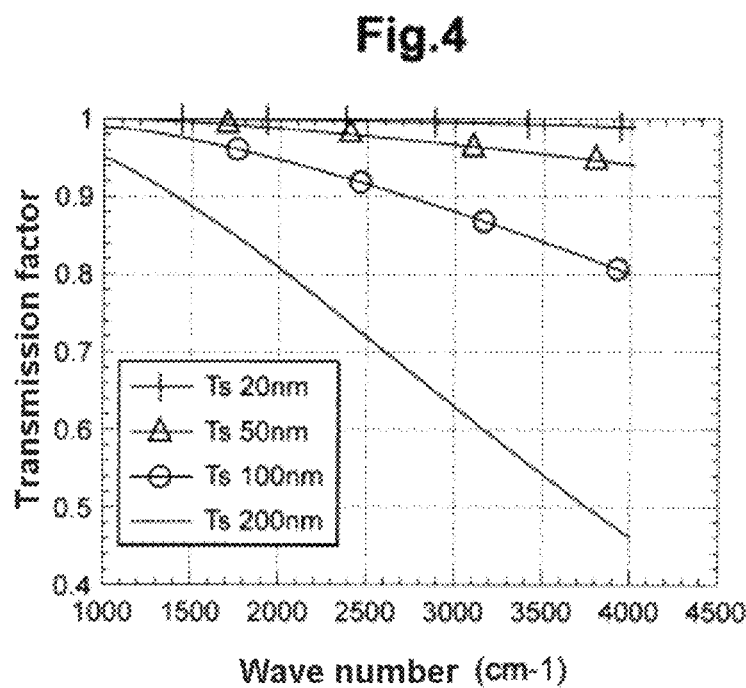
FIG. 4 illustrates the result curves of the numerical simulations showing the loss of optical transmittance between the silicon prisms and the silicon substrate according to the invention, as a function of the thickness of the air gap separating them, this for an angle $\alpha$ of 30° and a polarization of the infrared beam of type s.

The inventors have carried out numerical simulations to evaluate the loss of optical transmittance between a silicon prism 3 and a silicon substrate 1 as a function of the thickness Ts of the air gap for an angle α of 30° and an s polarization as a function of the wave number of the infrared beam. The results of these simulations are shown in the form of curves in FIG. 4. From these results, it may be concluded therefrom that an average thickness Ts of the air gap allowing good optical coupling may typically be of the order of a few tens of nanometers. Care is therefore taken to apply a sizable clamping load, so as to minimize this air gap. For example, a clamping torque of the order of 0.1 Nm is suitable.

Figure 5:
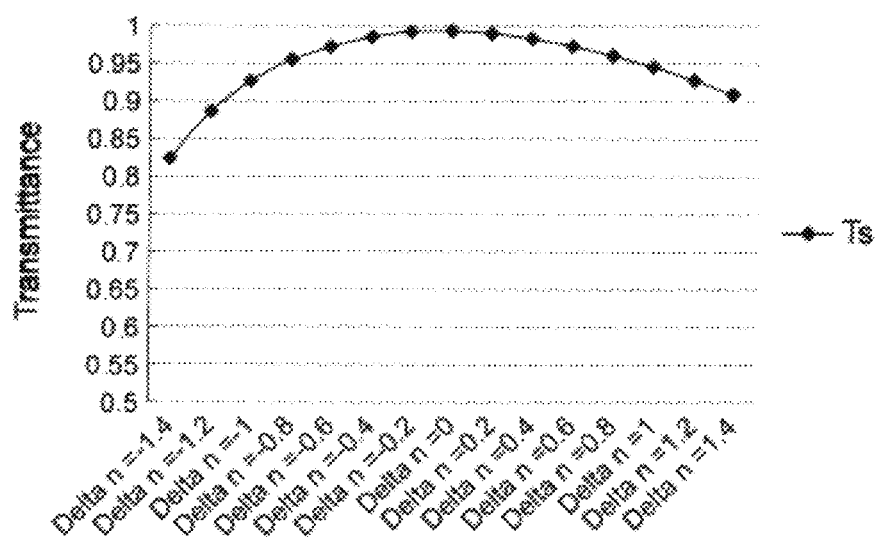
FIG. 5 illustrates the result curve of the numerical simulations showing the loss of optical transmittance at a wavelength of 2000 $cm^{-1}$ between the silicon prisms and the substrate according to the invention, as a function of the difference of their refractive indices, this for an angle $\alpha$ of 30° and a polarization of the infrared beam of type s.

The inventors also have carried out numerical simulations to evaluate the transmittance losses between prism and substrate and vice-versa, for a substrate made of a different material from that of the silicon prisms. The simulations have been undertaken at a wavelength of 2000 $cm^{-1}$ by varying the mismatch of optical index between prisms and substrate, while fixing the air gap Ts at 40 nm, the angle α being 30°, this for an s polarization. The results of these simulations are shown in curve form in FIG. 5. It is specified that on this curve Delta n signifies the difference of index between prisms 3, 4 and substrate 1. It is also specified that the transmittance under s polarization represented is equal to the product of the transmittance between the input prism 3 and the substrate 1 and that between the substrate 1 and the output prism 4. From this curve it is concluded therefrom that the transmittance losses are reasonable even for noticeable index differents since the loss is equal to 0.05 for an index mismatch of 0.8 and to 0.1 for an index mismatch of 1.4.

Once the optical coupling of the light is effective, the sample material 2 deposited on the front face 10 of the substrate 1 is probed at each reflection at the surface of this face, either by propagation of the light directly in the solid sample, or by an evanescent wave which is established after the diopter where the total reflection takes place, as is symbolized in FIG. 6. The infrared spectrum detected after travelling through the substrate 1 contains the information about the interaction of the infrared beam with the surface 10 of the substrate. In the case where the solid material of the sample is probed by an evanescent wave, the depth of this wave depends inter alia on the angle of propagation $\theta$. The closer the latter is to the critical angle $\theta c$ the larger the evanescent wave, hence making it possible to probe a thick sample layer 2.

Figure 7:
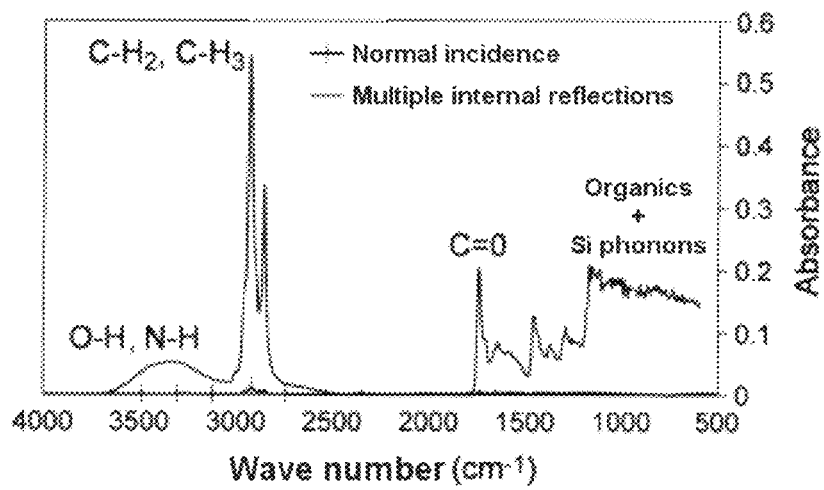
FIG. 7 illustrates the absorbance peaks obtained by infrared spectroscopy, at the surface of a bare silicon substrate respectively at normal incidence and by multiple internal reflections according to the method of the invention.

The advantage of such a configuration is the ability to probe the surface at each internal reflection. As a function of the angle $\alpha$ of the prisms 3, 4 and of the distance between the input prism 3 and output prism 4, it is possible to generate of the order of a hundred internal reflections. For example, it is possible to obtain a number equal to 108 internal reflections for a substrate 1 of thickness 800 μm, a distance between prisms 3, 4 of the order of 5 cm and an angle of propagation $\theta$ in the substrate of 30°. Thus, the measurement of a sample 2 by multiple internal reflections exhibits high sensitivity, of the same order as the number of internal reflections with respect to a conventional measurement by infrared transmission under normal incidence. This is illustrated in FIG. 7 where it is seen by comparison that the organic contamination at the surface of a silicon substrate is detected well by a measurement under multiple internal reflections according to the invention but hardly at all by the measurement under normal incidence.

To subject the solid sample layer 2 to a controlled environment, which is representative of in-situ conditions, in accordance with the invention, an element 6 that may be described as being a confinement cell is installed.

Figure 8:
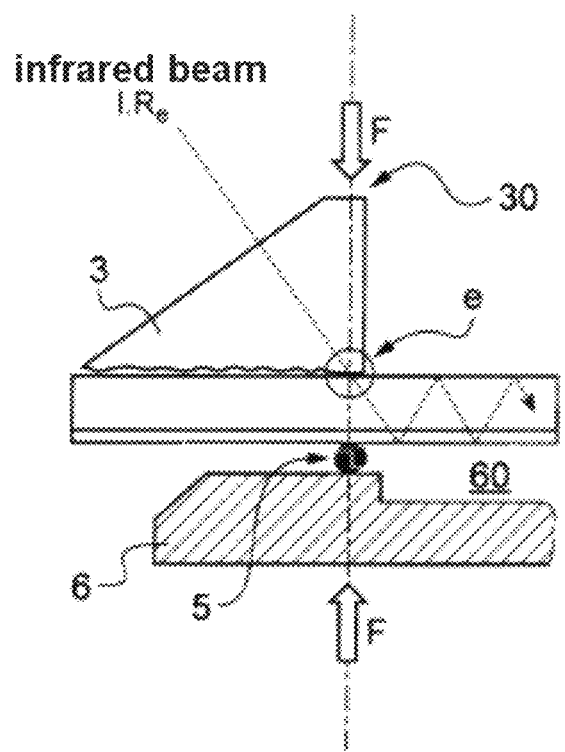
FIG. 8 is a cross-sectional schematic view of a device according to the first alternative of the invention showing the clamping of leaktightness and of optical coupling between a prism and the substrate according to a first variant of the invention.

Such a cell 6 comprises a chamber 60 with an aperture 61 rendered leaktight in relation to the outside by a peripheral O-ring seal 5 (FIG. 8). The sample layer 2 to be analyzed is placed facing the aperture 61 of the chamber 60 and then the prisms 3, 4 are clamped tight against the rear face 11 of the substrate 1 and retained with the aid of a clamping system, not represented. The clamping force, symbolized by the arrows F in FIG. 8, makes it possible at one and the same time to produce the optical coupling between the prisms 3, 4 and the substrate 1 and the actual leaktightness between the chamber 60 delimited by the layer 2 and the outside.

The O-ring seal 5 also facilitates the clamping of the prisms without breaking the substrate.

Figure 9:
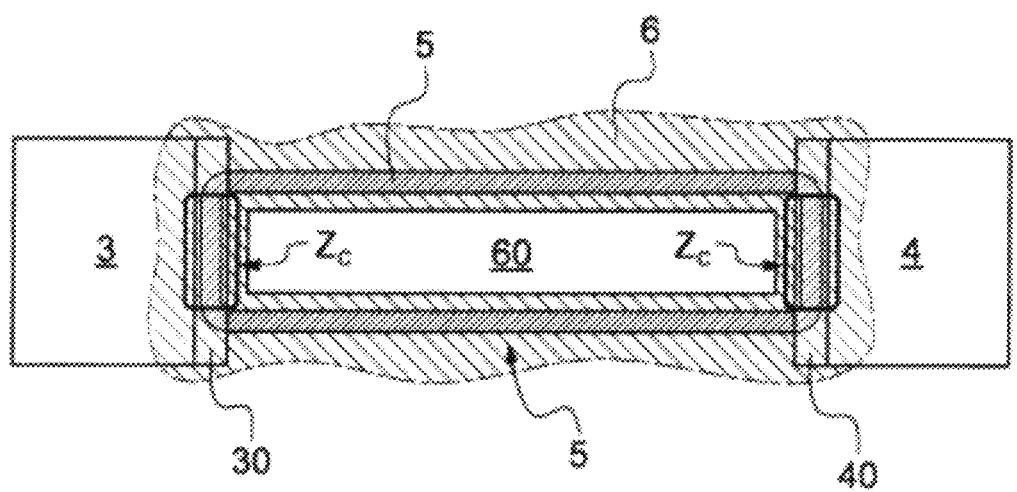
FIG. 9 is a view from above of the device according to FIG. 8 showing the relative arrangement between the various components of a device according to the invention.

In order to produce in an optimal manner the coupling respectively the decoupling of the light in the substrate and to propagate the light in the interaction zone Zi between sample layer 2 and fluid present in the chamber 60, the coupling zone Zc of the prism, a peripheral part of the O-ring seal 5 as well as the land 30, 40 of the input prism 3 respectively output prism 4 are aligned with the axis where the clamping force is applied, such as illustrated in FIGS. 8 and 9. This furthermore makes it possible to minimize the air gap between each of the prisms 3, 4 and the substrate 1 in this coupling zone Zc. Next, the infrared beam I.Re is aligned so as to reach the coupling zone Zc at the level of the interface between each prism 3, 4 and the substrate 1.

By way of variant, provision may be made to produce a decoupling between the clamping of the leaktight seal 5 and the clamping of the prisms 3,4. Such a variant is shown in FIGS. 10 and 11: provision is made to house a piece forming a bearing surface 50 in a groove of the cell 6 facing each prism 3, 4 land 30, 40. Stated otherwise, the lands 30, 40 are arranged offset from the peripheral seal 5 and plumb with the bearing surfaces 50. The clamping of the prisms 3, 4 is thus produced by back-reaction load of the clamping force on the front face 10 or the solid sample 2.

According to a first embodiment, the sample layer 2 may be subjected to a gas with controlled parameters. Provision may thus be made for a pumping system 90 associated with valves 80, 81 making it possible to evacuate the chamber 60 and the pipelines and feed aperture 62 and extraction apertures 63, before the actual feeding of the gas in a controlled manner so as to interact with the solid sample 2 in the interaction zone Zi (FIG. 12). One or more sensors 7 may be arranged on the cell 6 so as to control diverse parameters inside the chamber 60, such as pressure, temperature, composition etc.

Figure 13:
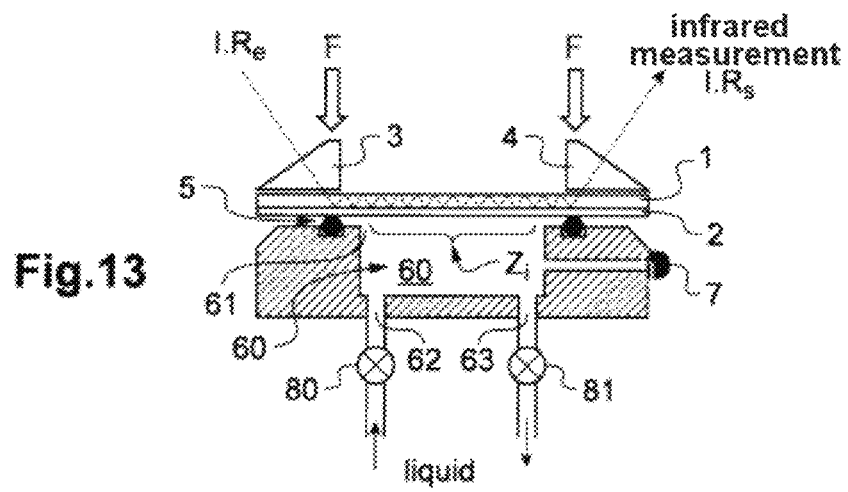
FIG. 13 is a schematic side view showing a device according to the first alternative of the invention and making it possible to subject the solid sample layer to a controlled liquid environment.

According to a second embodiment, the sample layer 2 may be subjected to a liquid with controlled parameters. A feed extraction system with suitable valves 80, 81 thus makes it possible to circulate liquid in a controlled manner so as to interact with the sample 2 (FIG. 13). One or more sensors 7 may be arranged on the cell 6 so as to control diverse parameters inside the chamber 60, such as pH, temperature, composition etc.

Figure 14:
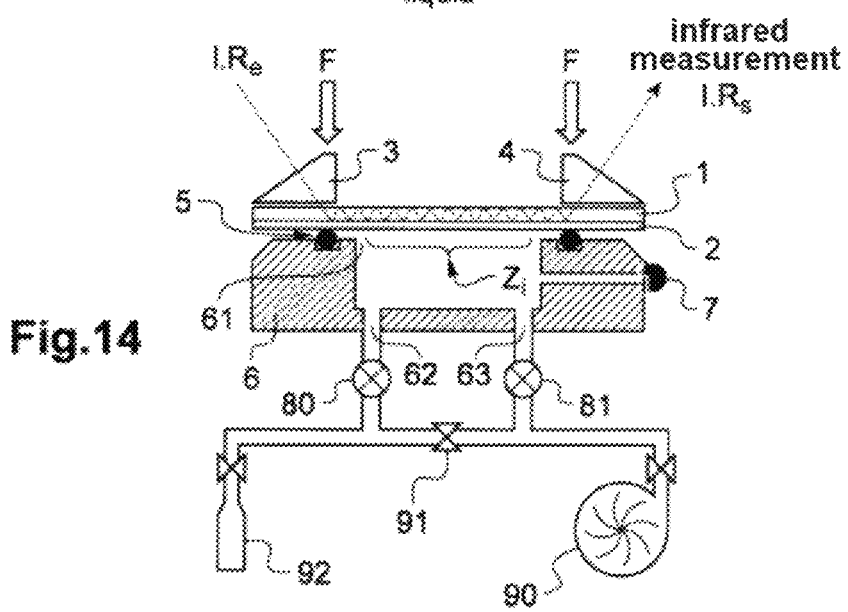
FIG. 14 is a schematic side view showing a first variant of gas feed of a device according to FIG. 12.

A first variant embodiment of the cell 6 under gas is shown in FIG. 14. According to this variant, the gas is generated from a reservoir of liquid 92 which evaporates when the chamber 60 and the pipelines are under vacuum.

Figure 15:
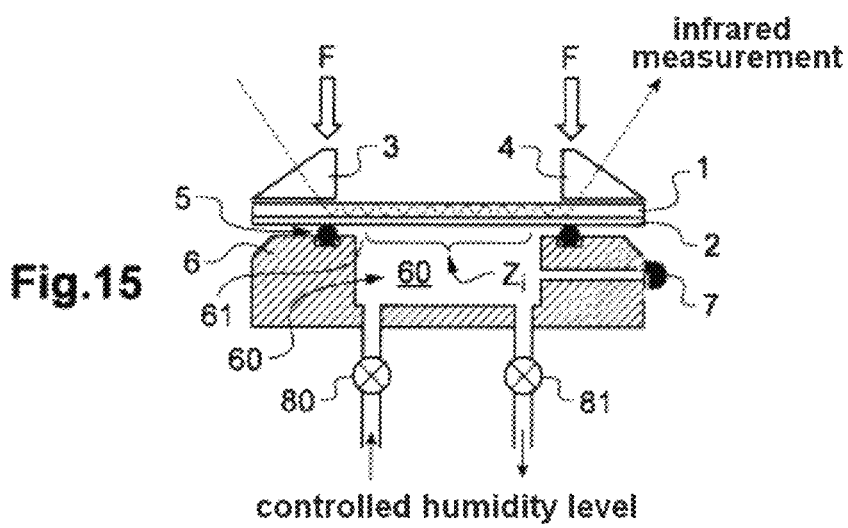
FIG. 15 is a schematic side view showing a second variant of gas feed of a device according to FIG. 12.

A second variant embodiment consists in injecting into the chamber 60 a carrier gas more or less saturated with moisture and to control the humidity factor thereof (FIG. 15).

Figure 16:
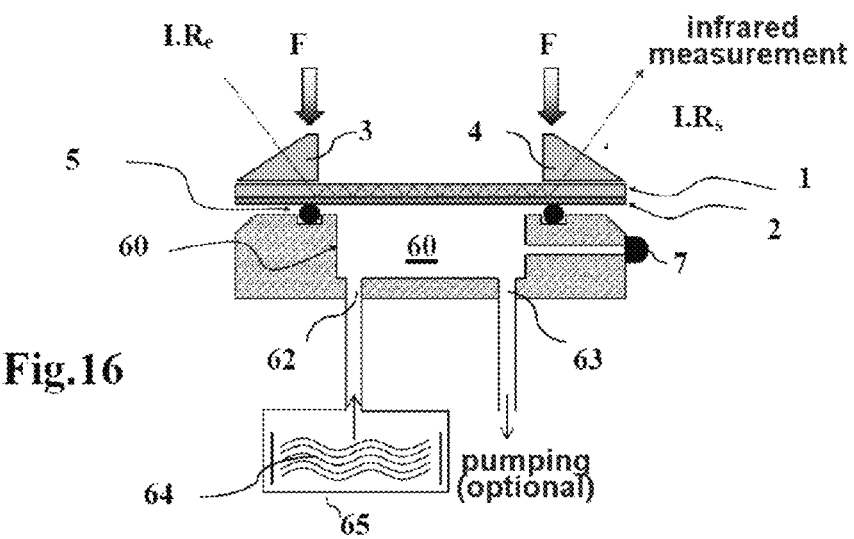
FIG. 16 is a schematic side view showing a device according to a third variant of the invention and making it possible to subject the solid sample layer to a plasma, the plasma being generated in an off-site manner with respect to the chamber.
Figure 17:
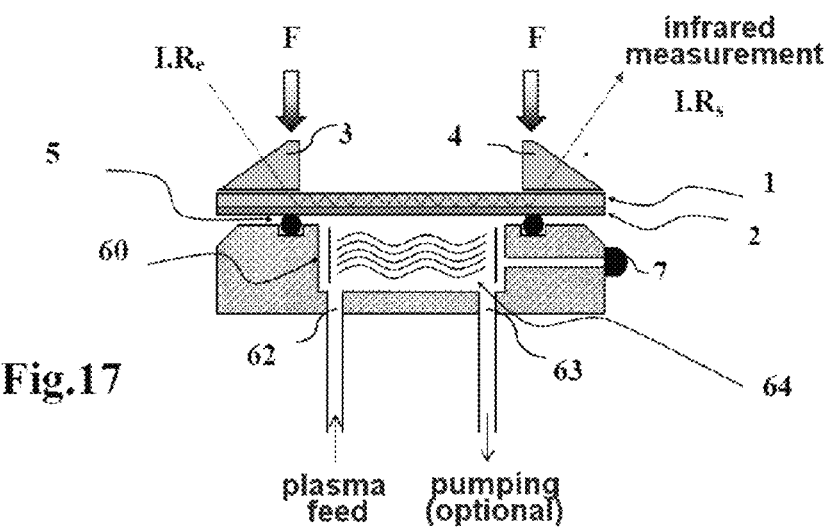
FIG. 17 is a schematic side view showing a device according to the third variant of the invention and making it possible to subject the solid sample layer to a plasma, the plasma being generated directly within the chamber.

According to a third variant embodiment, the sample layer 2 may be subjected to an environment consisting of reactive species. The reactive species (radicals) may arise from a plasma 64 or from an interaction of molecules with a heated filament, so that they interact with the surface. The plasma may be established in an off-site manner, that is to say generated in a generator of reactive species 65 remote from the chamber 60 and in communication with it through the pipelines and feed aperture 62 (FIG. 16). Alternatively, the plasma 64 may be generated directly in the chamber 60 (FIG. 17): in this case, ions and ultraviolet radiation are also present, in addition to the radicals of the plasma 64. The chamber 60 may be under vacuum or at atmospheric pressure in the case of an atmospheric plasma. Advantageously, the solid sample layer 2 may be conducting and serve as one of the electrodes for generating the plasma, thus favoring the ion bombardment at the surface of the sample 2.

Figure 18:
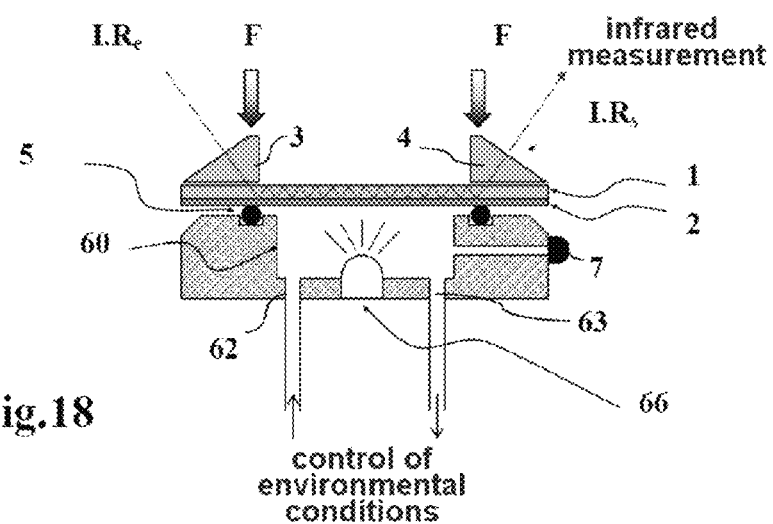
FIG. 18 is a schematic side view showing a device according to another variant of the invention according to which the chamber with controlled environment is furthermore illuminated by a luminous source.

Another variant of the invention illustrated in FIG. 18 consists in using an illumination system 66 which illuminates the inside of the chamber 60. This system 66 may or may not be coupled with the system for controlling the environmental conditions inside the chamber 60. The illumination system may advantageously be an ultraviolet light (UV) which thus favors the decontamination or the sterilization of the surfaces and in particular that of the sample 2. The system 66 may also be an infrared light so as to cause heating of the surface of the sample 2. The luminous source 66 may be monochromatic (laser) or have a wide emission range.

A second alternative according to the invention is shown in FIG. 19. Instead of the prisms 3, 4, provision may be made to bevel the edges of the substrate 1 between its front face 10 and its rear face 11. The bevels obtained 12, 13 make it possible to trap the infrared light in the substrate 1 and to cause it to undergo multiple internal reflections (FIG. 19).

A third alternative according to the invention is shown in FIG. 20. Instead of the prisms 3, 4, or bevels 12, 13, provision may be made for a substrate 1 with two rounded edges 14 between its front face 10 and its rear face 11. The roundings 14 make it possible to trap the infrared light in the substrate 1 and to cause it to undergo multiple internal reflections (FIG. 20). According to these second and third alternatives, care is taken that the seal 5 clamping system does not modify the internal reflection condition by moving it away from the vicinity of the optical beam.

Only relative measurements of absorption with respect to a reference measurement, for example the bare substrate or the first measurement under vacuum, can be carried out, for each controlled environment condition, using the device as described with reference to FIGS. 1 to 20.

These measurements can be improved by carrying out absolute measurements of absorption by subtracting at each condition two measurements having a different optical path.

Stated otherwise, this entails carrying out two consecutive measurements with different angles of propagation. Accordingly, two pairs of prisms of different nature or angle can be arranged on the rear face 11 of the substrate 1 in parallel.

Such an advantageous mode with two pairs of prisms respectively 3a, 4a and 3b, 4b of different angle is shown in FIG. 21. Thus the prisms 3a, 4a have an angle equal to 20° while the prisms 3a, 4b have an angle equal to 45°. At equal distance between two prisms, the optical path difference will depend just on the angle of propagation in the substrate 1.

A measurement for each angle of propagation is carried out at each condition of controlled environment in the chamber 60. Next, the measurement made with the smallest angle of propagation is normalized, that is to say is referenced, by that made with the largest angle so as to obtain the absolute measurement (auto-referenced) of the infrared absorption of the sample layer 2.

According to this mode, the pair of prisms 3a, 4a; 3b, 4b is advantageously selected without there being any need to realign the optical beam between the measurements. For example, by mounting two pairs of silicon prisms respectively of 20° and 45° on a substrate 1 aligned for propagation prisms equal to 30°, two angles of propagation of respectively 22.9° and 40.7° are obtained. Moreover, care is taken that the device according to this mode with two prism pairs takes into account the previously described constraints of optical coupling of the light, that is to say essentially the refraction of the beam in the right angle of the input prism 3 and the clamping on the axis of this right angle.

The invention which describes allows controlled-environment optical analysis of a solid sample layer 2 deposited on the front face 10 of the substrate 1. Instead of a layer, provision may be made for a surface preparation and/or conditioning of the front face 10 of a substrate, for example by cleaning, etching, etc. to analyze the interaction thereof with a controlled environment.

Other variants and improvements may be envisaged without however departing from the scope of the invention.

The invention is not limited to the examples which have just been described; in particular, characteristics of the examples illustrated may be combined together within variants that are not illustrated.

REFERENCES CITED

[1]: M. Olivier, N. Rochat, et al.: « *Infrared Study of Hydrogen in Ultra-Thin Silicon Nitride Films Using Mutiple Internal Reflection Spectroscopy (MIR) in 200 mm Silicon Wafers*» (1999), Physica Status Solidi A175 (1): 137-143;
[2]: N. Rochat, M. Olivier, et al.: « *Multiple internal reflection Infrared Spectroscopy using two prism coupling geometry: A convenient way for quantitative study of organic contamination on silicon wafers*» (2000), Applied Physics Letters 77(14): 2249-2251;
[3]: N. J. Harrick: « Internal Reflection Spectroscopy», Book Chapter 4, Harrick Scientific corporation.

The invention claimed is:

1. A method of preparation and optical analysis of a solid sample, by multiple internal reflection infrared spectroscopy comprising:
    obtaining at least one substrate that is transparent to infrared light and comprises at least a main front face and a main rear face;
    producing at least one solid sample on the main front face of the substrate;
    once the solid sample has been deposited, installing around at least one part of the main front face of the substrate or of the solid sample an element comprising a chamber having an aperture that opens onto and is delimited by the main front face of the substrate or by the solid sample and that defines a leaktight interaction zone (Zi) in relation to the outside of the chamber;
    feeding the chamber with a liquid, a gas, or reactive species with controlled parameters to control an environment in the leaktight interaction zone;
    sending an infrared light beam through the substrate; and
    recovering the beam after it has undergone multiple internal reflections in the substrate.

2. The method of claim 1, further defined as comprising:
    installing at least one pair of prisms remote from one another on the rear face of the substrate, wherein the angle (a) of the prisms is suitable to allow multiple internal reflections in the substrate of an infrared light refracted by one of the prisms;
    sending an infrared light beam through one of the prisms of a pair; and
    recovering the beam after it has undergone multiple internal reflections in the substrate and been re-emitted by the other prism of the pair.

3. The method of claim 2, wherein installing the element comprises clamping a peripheral O-ring seal around the aperture against the main front face of the substrate, wherein the clamping of the seal simultaneously presses the prisms against the rear face of the substrate.

4. The method of claim 3, wherein the prisms each comprise a land on a vertex opposite to the surface pressed against the rear face of the substrate and the axis of the clamping is aligned with the lands and the seal.

5. The method of claim 3, comprising:
    installing at least two pairs of prisms, wherein the angle of the prisms and/or one pair are composed of a material that is different from that of the other pair, and the two prisms of one pair are as equally distant from each other as the two prisms of the other pair;

sending an infrared light beam through one of the prisms of the first pair and recovering the beam after it has undergone multiple internal reflections in the substrate and been re-emitted by the other prism of the first pair; and sending an infrared light beam through one of the prisms of the second pair and recovering the beam after it has undergone multiple internal reflections in the substrate and been re-emitted by the other prism of the second pair.

6. The method of claim 1, further defined as comprising: beveling at least two edges of the substrate between the main front face and the main rear face, wherein the angle of the bevels is suitable to allow multiple internal reflections in the substrate of an infrared light refracted by one of the bevels;

sending an infrared light beam through one of the beveled edges of the substrate; and recovering the beam after it has undergone multiple internal reflections in the substrate and been re-emitted by the other beveled edge of the substrate.

7. The method of claim 1, further defined as comprising: providing the substrate with at least two rounded edges between the main front face and the main rear face, wherein the rounded edges are suitable to allowing multiple internal reflections in the substrate of an infrared light refracted by one of the edges;

sending an infrared light beam through one of the rounded edges of the substrate; and recovering the beam after it has undergone multiple internal reflections in the substrate and been re-emitted by the other of the rounded edge of the substrate.

8. The method of claim 1, wherein the feeding of the chamber is with a liquid, the temperature and/or pressure and/or pH and/or composition of which are/is controlled.

9. The method of claim 1, wherein the feeding of the chamber is with a gas, the temperature and/or pressure and/or humidity factor of which are/is controlled.

10. The method of claim 9, comprising evacuating the chamber before feeding it with the gas.

11. The method of claim 10, wherein the gas is fed from a reservoir of liquid which evaporates in the chamber.

12. The method of claim 10, wherein the gas has a humidity factor that is controlled in the chamber.

13. The method of claim 10, wherein the feeding is carried out with a reactive species that is controlled in the chamber.

14. The method of claim 13, wherein the reactive species is a plasma.

15. The method of claim 1, further defined as a method of analyzing of a sample of porous material subjected to an environment with controlled humidity factor.

16. The method of claim 15, wherein the porous material is an hydrogenated oxidized silicon carbon SiOCH.

17. A device for the preparation and optical analysis of a solid sample by multiple internal reflection infrared spectroscopy, the device comprising:

a substrate comprising at least one main front face, at least one main rear face, and at least one deposited solid sample on the main front face; and an element comprising a chamber having an aperture that opens onto and is delimited by the main front face of the substrate or by the solid sample on the main front face of the substrate and that defines a leaktight interaction zone (Zi) in relation to the outside of the chamber, wherein the chamber is suitable for being fed with a liquid, a gas, or reactive species with controlled parameters so as to control an environment in the leaktight interaction zone during use.

18. The device of claim 17, further comprising at least one pair of prisms arranged remote from one another and at least in part on the rear face of the substrate, wherein the angle of the prisms are suitable for allowing multiple internal reflections in the substrate of a refracted infrared light by one of the prisms during use.

19. The device of claim 18, wherein each of the prisms comprise a land on a vertex.

20. The device of claim 19, further comprising a peripheral O-ring seal housed in a peripheral groove around the aperture of the element.

21. The device of claim 18, further defined as comprising two pairs of prisms, the angle of the prisms and/or the material of one pair being different from that (those) of the other pair, the distance between the two prisms of one pair being equal to that between the two prisms of the other pair.

22. The device of claim 21, wherein the substrate and the pairs of prisms comprise silicon, the angle (a) of the prisms of one pair being equal to 20°, and the angle of the prisms of the other pair being equal to 45°.

23. The device of claim 18, wherein the angle (a) of the prisms of a pair is between 20° and 60°.

24. The device of claim 17, wherein the substrate comprises at least two bevels between the main front face with an angle of the bevels being suitable to allow multiple internal reflections in the substrate of an infrared light refracted by one of the bevels during use.

25. The device of claim 17, wherein the substrate comprises at least two rounded edges between the main front face and the main rear face with the rounding of the edges being suitable to allow multiple internal reflections in the substrate of an infrared light refracted by one of the edges during use.

26. The device of claim 17, further comprising a peripheral O-ring seal housed in a peripheral groove around the aperture of the element.

27. The device of claim 17, further comprising one or more sensors suitable for measuring the pressure and/or the temperature and/or the pH and/or the humidity inside the chamber.

28. The method of claim 1, wherein installing the element comprises clamping a peripheral O-ring seal around the aperture against the main front face of the substrate.

29. A method of preparation and optical analysis of a prepared surface of a main front face of a substrate and/or a conditioned main front face of a substrate, by multiple internal reflection infrared spectroscopy comprising:

obtaining at least one substrate that is transparent to infrared light and comprises at least a main front face and a main rear face;

preparing the surface of the main front face of the substrate and/or conditioning the main front face of the substrate, once the surface of the main front face of the substrate has been prepared and/or the main front face of the substrate has been conditioned, installing around at least one part of the main front face of the substrate an element comprising a chamber having an aperture that opens onto and is delimited by the main front face of the substrate and that defines a leaktight interaction zone (Zi) in relation to the outside of the chamber;

feeding the chamber with a liquid, a gas, or reactive species with controlled parameters to control an environment in the leaktight interaction zone;

sending an infrared light beam through the substrate; and recovering the beam after it has undergone multiple internal reflections in the substrate.

30. A device for the preparation and optical analysis of a prepared surface of a main front face of a substrate and/or a conditioned main front face of a substrate, by multiple internal reflection infrared spectroscopy the device comprising:
- a substrate comprising at least one main front face, at least one main rear face, and a prepared surface of the main front face and/or a conditioned main front face;
- an element comprising a chamber having an aperture that opens onto and is delimited by the main front face of the substrate and that defines a leaktight interaction zone (Zi) in relation to the outside of the chamber, wherein the chamber is suitable for being fed with a liquid, a gas, or reactive species with controlled parameters so as to control an environment in the leaktight interaction zone during use.

* * * * *